US011865326B1

(12) United States Patent
Herbst et al.

(10) Patent No.: US 11,865,326 B1
(45) Date of Patent: Jan. 9, 2024

(54) HIGH PRECISION, MULTI-OUTPUT PULSE AND/OR SIGNAL GENERATORS

(75) Inventors: Ewa Herbst, Edgewater, NJ (US); Lisa A. Schmidt, Sparta, NJ (US)

(73) Assignee: Innovations Holdings, L.L.C., Edgwater, NJ (US)

( * ) Notice: Subject to any disclaimer, the term of this patent is extended or adjusted under 35 U.S.C. 154(b) by 495 days.

(21) Appl. No.: 11/063,195

(22) Filed: Feb. 22, 2005

Related U.S. Application Data

(63) Continuation-in-part of application No. 10/706,844, filed on Nov. 12, 2003, now abandoned, which is a continuation of application No. 09/507,873, filed on Feb. 22, 2000, now Pat. No. 6,684,106, which is a continuation of application No. 09/013,049, filed on Jan. 27, 1998, now Pat. No. 6,029,090.

(60) Provisional application No. 60/546,276, filed on Feb. 20, 2004, provisional application No. 60/034,869, filed on Jan. 27, 1997.

(51) Int. Cl.
*A61N 1/02* (2006.01)
*A61N 1/36* (2006.01)

(52) U.S. Cl.
CPC .................. *A61N 1/3603* (2017.08)

(58) Field of Classification Search
CPC ........... A61N 1/025; A61N 1/08; A61N 1/378
USPC ............................ 607/48; 327/121, 396, 276
See application file for complete search history.

(56) References Cited

U.S. PATENT DOCUMENTS

| | | | | |
|---|---|---|---|---|
| 3,294,092 A | * | 12/1966 | Landauer ................. | A61N 1/32 607/66 |
| 4,404,522 A | * | 9/1983 | Pucciarello ................... | 324/114 |
| 4,499,549 A | * | 2/1985 | Bartlett ..................... | G06J 1/00 708/2 |
| 4,774,967 A | | 10/1988 | Zanakis et al. | |
| 4,919,140 A | | 4/1990 | Borgens et al. | |
| 5,006,773 A | * | 4/1991 | Goldberg ...................... | 318/696 |
| 5,041,974 A | * | 8/1991 | Walker ............... | A61N 1/36034 607/63 |

(Continued)

*Primary Examiner* — Alyssa M Alter
(74) *Attorney, Agent, or Firm* — Byrne Poh LLP

(57) ABSTRACT

A multi-functional electrical stimulation (ES) system adapted to yield output signals for effecting faradic, electromagnetic, or other forms of electrical stimulation for a broad spectrum of different biological and bio-medical applications. The system includes and ES signal stage having a selector coupled to a plurality of different signal generators, each generator producing a signal having a distinct shape such as a sine, a square or sawtooth wave or a simple or complex pulse form, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can adjust it to yield an electrical stimulation signal of whatever type he wishes and can then observe the effects of this signal on a substance being treated.

9 Claims, 7 Drawing Sheets

(56) References Cited

U.S. PATENT DOCUMENTS

| | | | |
|---|---|---|---|
| 5,549,656 A * | 8/1996 | Reiss | 607/48 |
| 5,800,465 A * | 9/1998 | Thompson | A61N 1/368 |
| | | | 607/9 |
| 2005/0216062 A1* | 9/2005 | Herbst | 607/2 |

* cited by examiner

To Fig. 6b

HIGH PRECISION, MULTI-OUTPUT PULSE AND/OR SIGNAL GENERATORS

CROSS-REFERENCE TO RELATED APPLICATIONS

This application claims priority under 35 U.S.C. § 119(e) to U.S. Provisional Patent Application No. 60/546,276, filed Feb. 20, 2004, which is hereby incorporated by reference herein in its entirety. This application is also a continuation-in-part of U.S. patent application Ser. No. 10/706,844, filed on Nov. 12, 2003, and to which this application claims priority under 35 U.S.C. § 120. U.S. patent application Ser. No. 10/706,844 is a continuation of U.S. patent application Ser. No. 09/507,873, filed on Feb. 22, 2000, now U.S. Pat. No. 6,684,106, which is a continuation of U.S. patent application Ser. No. 09/013,049, filed Jan. 27, 1998, now U.S. Pat. No. 6,019,090, which claimed priority under 35 U.S.C. § 119(e) to U.S. Provisional Patent Application No. 60/034,869, filed on Jan. 27, 1997, all of which are incorporated by reference herein in their entireties.

STATEMENT REGARDING FEDERALLY SPONSORED RESEARCH OR DEVELOPMENT

The government may have certain rights in the present invention pursuant to a grant from the National Institute of Neurological Disorders and Stroke (NINDS), which is part of the National Institute of Health (NIH), Grant No. 3R44NS34218-03S1.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF INVENTION

1. Field of Invention

This invention relates generally to the electrical stimulation devices for effecting faradic, electromagnetic or other forms of electrical stimulation, and more particularly, to a multi-functional system for this purpose capable of selectively yielding electrical stimulation signals for a broad spectrum of different biological and bio-medical applications as well as for other applications, such as electrophoresis.

2. Status of Prior Art:

Electrical stimulation (ES) is widely used in biological and bio-medical research as well as in diagnostics and in clinical treatment. In faradic stimulation an intermittent or a continuous direct or alternating current or voltage is produced, whereas in electromagnetic stimulation, a current passing through a coil produces an electromagnetic field whose pattern depends on the wave form of the current.

Electrical stimulation is employed to effect nerve regeneration, in neuromuscular research, in medical diagnosis and treatment, and in pulsed voltage electrophoresis. Such stimulation is also used in bone healing and in wound healing, as well as in pain relief by means of transcutaneous electrical nerve stimulation (TENS). The use of ES to effect nerve regeneration is disclosed in the Zanakis et al. U.S Pat. No. 4,774,967 as well as in the Borgens U.S. Pat. No. 4,919,140.

Researchers in the biological and medical sciences, physiotherapists, and clinicians who make use of ES require electrical stimulators of a type suitable for the activities in which they are engaged. Thus neurological investigators who seek to non-invasively stimulate deep nerves make use of commercially available magnetic stimulators which produce a high-intensity magnetic field pulse for this purpose.

Also commercially available are constant current stimulators for direct cortical stimulation as well as electrical stimulators for nerve and muscle stimulation procedures which generate single or double pulses, or trains of such pulses. And commercially available are wave generators capable of selectively generating sine and square wave pulses suitable for other types of electrical stimulation.

But what is not available to researchers and others who make use of electrical stimulation is a multi-functional system capable of yielding an electrical stimulation signal that is appropriate for whatever biological or biomedical application is the concern of the user of the system.

Let us assume, by way of example, that a researcher is engaged in a neurological research program in the course of which it becomes necessary to conduct tests on the effects of many different types of electrical stimuli on a certain set of nerves. The researcher would then have to assemble from different commercial sources the several electrical stimulators of different types called for by this program. This burdensome requirement adds substantially to the cost of conducting this research and to its space demands.

While the invention will be described herein as a system for producing electrical stimulating signals, the signals produced thereby can also be used for electroporation, electrophoresis (preferably pulsed voltage electrophoresis) and iontophoresis as well as for electrochemical applications as in the treatment of cancer in which a current is passed through the tissue being treated. The signals can also be used for transdermal drug delivery.

SUMMARY OF INVENTION

In view of the foregoing, the main object of this invention is to provide a multi-functional electrical stimulation (ES) system adapted to yield output signals for effecting faradic, electromagnetic or other forms of electrical stimulation for a broad spectrum of different biological and biomedical applications.

A significant advantage of a system in accordance with the invention is that it affords its user, whether a researcher, a diagnostician or a clinician, with whatever electrical stimulation signal is dictated by the specific type of electrical stimulation that is required. Thus if in conducting tests, a researcher needs to subject certain nerves to many different forms of electrical stimulation, the self-sufficient system, by itself and without accessories, is capable of supplying whatever electrical stimulation signals are appropriate.

Also an object of this invention is to provide a multi-functional system of the above type that includes a measuring stage that measures and displays the electrical stimulation signal operating on the substance being treated and also indicates and displays signals issuing from sensors which sense conditions prevailing in the substance, such as pH and $O_2$, whereby the user of the system is able to observe and monitor the effects of the electrical stimulation signal he has selected.

Another object of this invention is to provide a highly-compact system of the above type which can be manufactured at relatively low cost.

Briefly stated, these objects are attained by a multi-functional electrical stimulation (ES) system adapted to yield output signals for effecting faradic, electromagnetic or other forms of electrical stimulation for a broad spectrum of different biological and bio-medical applications. The system includes an ES signal stage having a selector coupled to a plurality of different signal generators, each producing a signal having a distinct shape such as a sine, a square or sawtooth wave, or a simple or complex pulse, the parameters of which are adjustable in regard to amplitude, duration, repetition rate and other variables.

The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

In another embodiment of the system, the signals from the ES signal stage are put on a bus from which they can be accessed by the output stages.

The electrical stimulation signal yielded by the system can be used for applications other than those involving electrical stimulation, such as for electrophoresis and electroporation. Or the signals from the system can be used in applications requiring mechanical or acoustic waves by applying the signal to an appropriate transducer.

BRIEF DESCRIPTION OF DRAWINGS

For a better understanding of the invention, as well as other objects and further features thereof, reference is made to the following detailed description to be read in conjunction with the accompanying drawing, wherein.

DETAILED DESCRIPTION OF INVENTION

Figure 1:
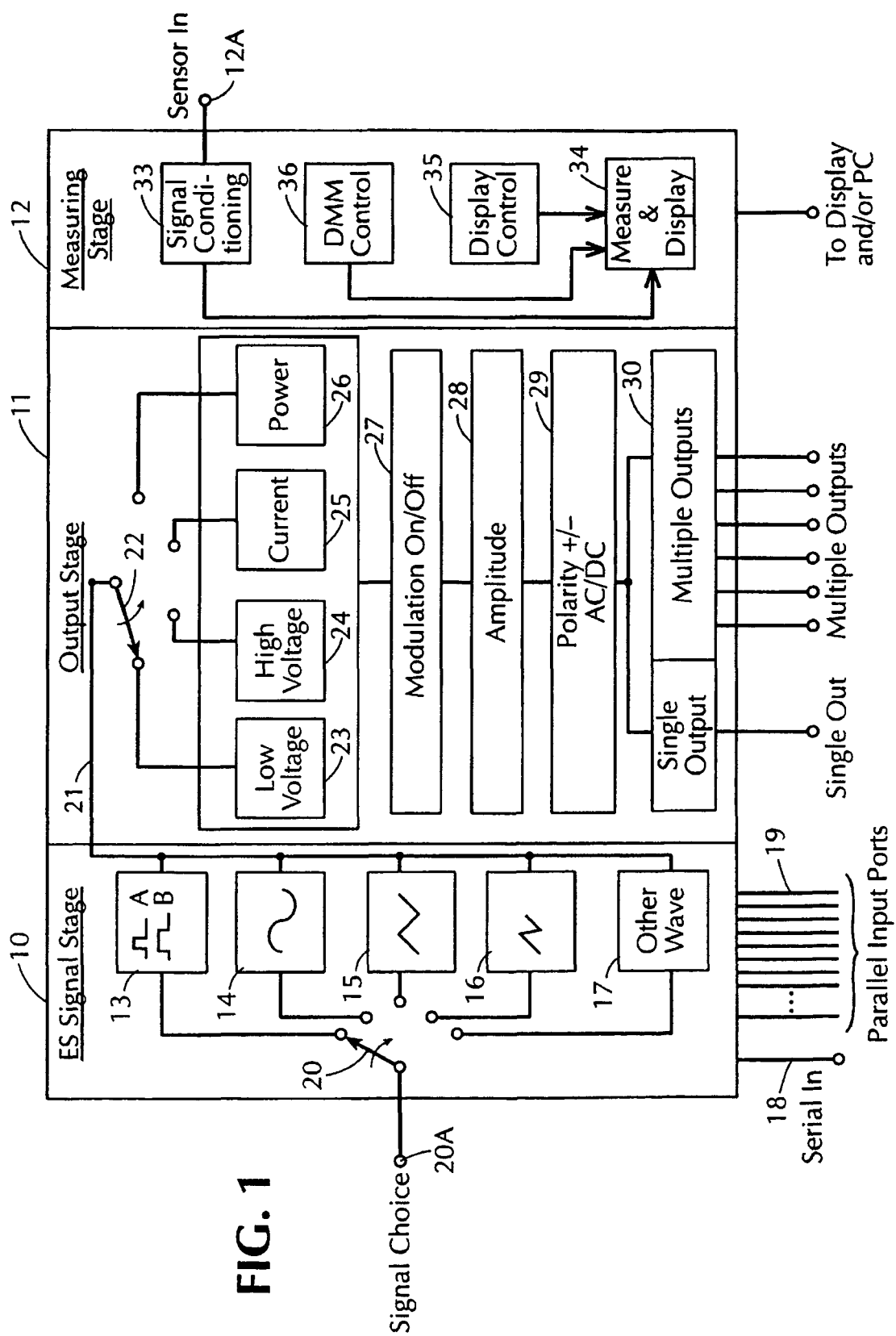
FIG. 1 is a block diagram of a system in accordance with the invention having an ES stage, an output stage and a measuring stage.

A system in accordance with the invention, as shown in FIG. 1, is composed of an ES signal stage 10, which at the user's discretion generates a faradic, an electromagnetic or other type of electrical stimulation signal, which is fed to an output stage 11. Output stage 11 processes the electrical stimulation signals selected by the user to yield a stimulation signal suitable for its intended biological or bio-medical application.

Also provided is a measuring stage 12 which measures and displays the electrical stimulation signal operating on the biological, substance being subjected thereto, and/or its electrical parameters as well as the output of various sensors which sense conditions prevailing in this substance whereby the user is able to observe, monitor as well as to adjust the effects of the stimulation signal he has selected on the substance being treated.

ES signal stage 10 includes signal generators 13 to 17 producing signals of different shape. Generator 13 is a pulse wave generator generating one or more rectangular pulses, such as pulses A and B of different width which can be outputted separately or can be added or subtracted from each other to yield A or B, A plus B or A minus B. Generator 14 is a sine wave generator, generator 15 generates a triangular or sawtooth wave, and generator 16 produces a ramp voltage wave. Generator 17 yields a wave of any arbitrary shape. The signal generators are capable of generating a minimum one pulsatory signal or a greater numbers of pulsatory signals, or of generating a gated signal with a minimum of one period or a greater number of periods, with individual adjustments of electrical parameters.

By means of a serial input port 18 to ES stage 10 or a set of parallel input ports 19, the parameters of the respective waves produced by signal generators 13 to 17 can be adjusted in frequency, pulse width, amplitude and repetition rate, or with respect to any other variable. Coupled to generators 13 to 17 and activated by a signal applied thereto at terminal 20A is a mechanical or electronic selector switch 20. The output signal from the signal generator selected by a switch 20 is applied through a line 21 to output stage 11. In practice, the line is preferably a bus system.

The ES signal stage 10 is preferably miniaturized and may take the form of a hybrid device or a single ASIC chip (Application Specific Integrated Circuit). Output stage 11 includes a mechanical or electronic selector switch 22 which applies the ES signal from stage 10 either to a low voltage processor 23, a high voltage processor 24, a current processor 25, or a power processor 26 to put the ES signal in a form appropriate to the intended application for electrical stimulation. In a preferred version, all signals can be accessed simultaneously by one or more output stages through a system bus. In practice, a combination of one or more signal generators in the ES signal stage with one or more of the output stages can be miniaturized.

The output of the processor 23, 24, 25 or 26 chosen by selector switch 22 is fed to a modulator 27 coupled to an amplitude control unit 28 which modifies the amplitude of the signal applied thereto. The output of amplitude-control unit 28 is applied to a polarity control unit 29 in which the electrical stimulation signal is given a positive or negative polarity or is converted to an AC signal, depending on the intended application for the electrical stimulation signal.

Each output stage can be configured with either multiple output terminals 30 or with a single output. The multiple outputs make it possible to run several parallel experiments or processes concurrently.

Figure 2:
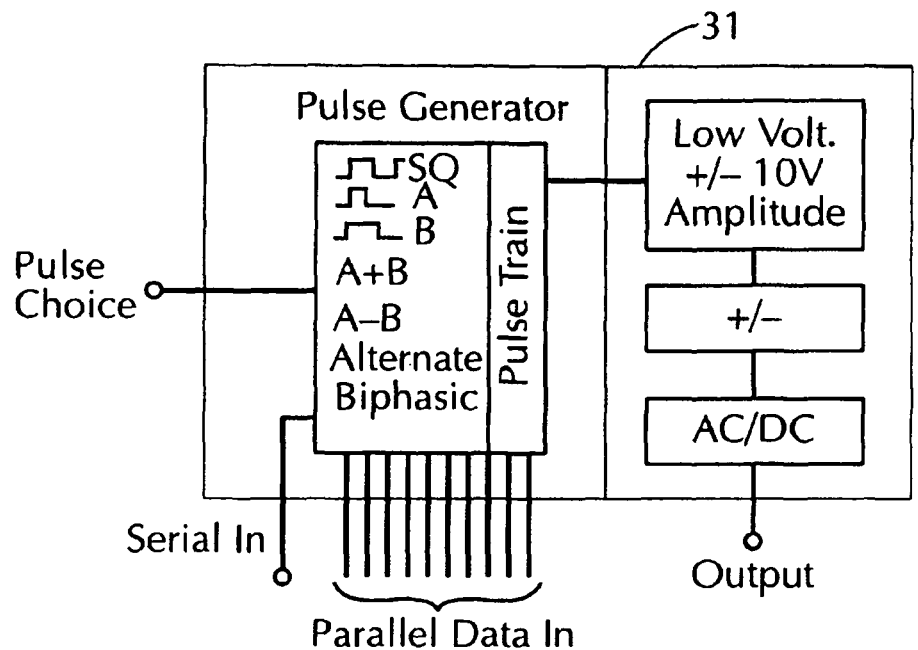
FIG. 2 is a block diagram of a basic version of a system for producing various electrical stimulation pulses.
Figure 3:
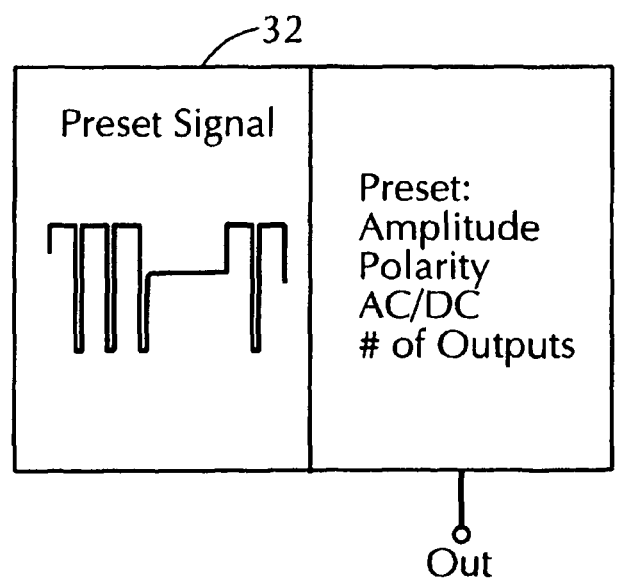
FIG. 3 illustrates an example of a preset custom module.

As previously mentioned, the ES system can be miniaturized to form a single ES component comprising signal generators and miniaturized output circuitry packaged together. A functional sketch of one such ES component 31 is shown in FIG. 2, and an example of a customized module 32 with a preset waveform and preset electrical parameters is shown in FIG. 3.

A preferred version of the ES component includes a sophisticated digital pulse generator on a chip and an analog circuitry to define complex pulse patterns, with amplitudes up to ±10V. The output can be fed into any number of desirable output stages, which can be integrated into the same component or be independent proprietary devices, e.g., voltage controlled or current controlled output stages with various voltage/current amplitudes, high frequency output stage with various bandwidths depending on a specific application, various power output stages, etc. Waveforms other than pulse patterns, as well as modulated signals can be part of such a "system on a chip."

The design of a digital ASIC consists of several blocks, which can be either used together to create a sophisticated pulse generator for biomedical applications, or can be used in any number of other applications requiring a pulse signal. Each of these blocks or functional modules can provide an independent waveform or pulse (A pulse; B pulse; square wave; time delay; etc). A basic one output version of the signal generator delivers two independent pulses A and B with digitally adjustable pulse widths, the same pulse repetition rate, and with an adjustable delay between them or for each of them. It also delivers a square wave and timing for alternate and biphasic pulses and two pulse trains. In a two or more output version, individual pulses can have independently set repetition rates.

Several of these independent signal generators can be combined into a multi-output device. All timing parameters of the pulses preferably are fully programmable by a user via hardware or via software-generated inputs. For example, one can adjust timing using thumbwheels or switches connected via parallel inputs of the ES component, or by using software and a serial, parallel, or custom interface as an input (or a combination of analog and digital inputs can be used). The ES component can include both a parallel and a serial interface so that the user can define the optimal means for each application.

The analog output amplitudes of the ES component or ES system can be adjusted for each pulse separately (via hardware or software, as above). At the same time, a specific DC level can be added; i.e., signal can be shifted up or down from zero line. The alternate and biphasic pulses are designed so that only one adjustment for both positive and negative pulse width and amplitude is required, which results in guaranteed symmetrical signals.

Figure 4A:
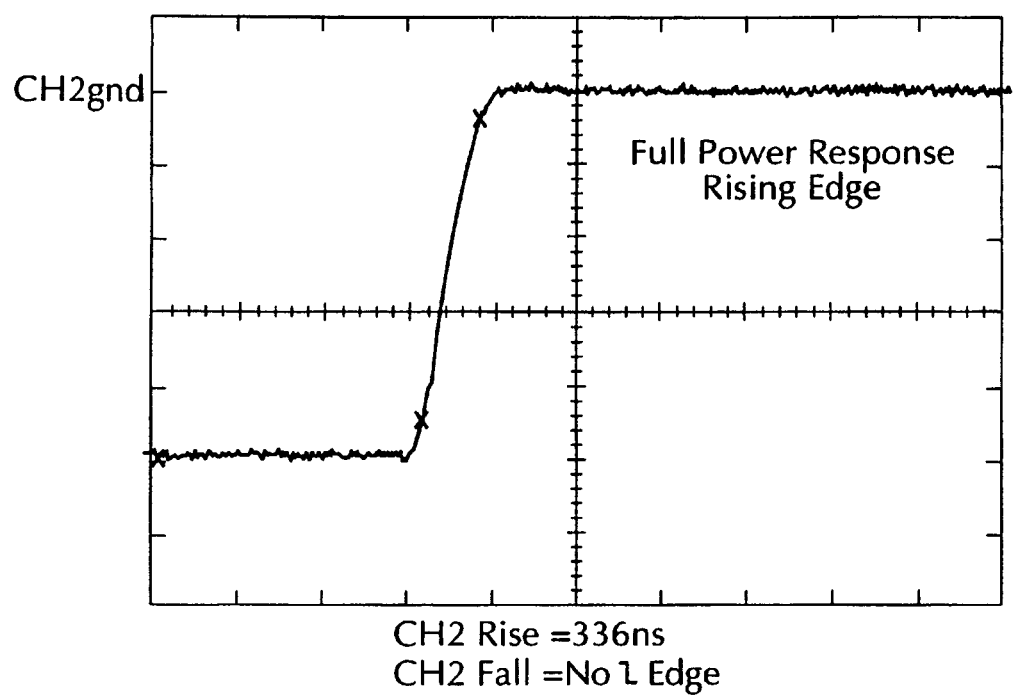
FIG. 4A is a graph showing at the full power output of an amplifier a pulse having a rising edge.
Figure 4B:
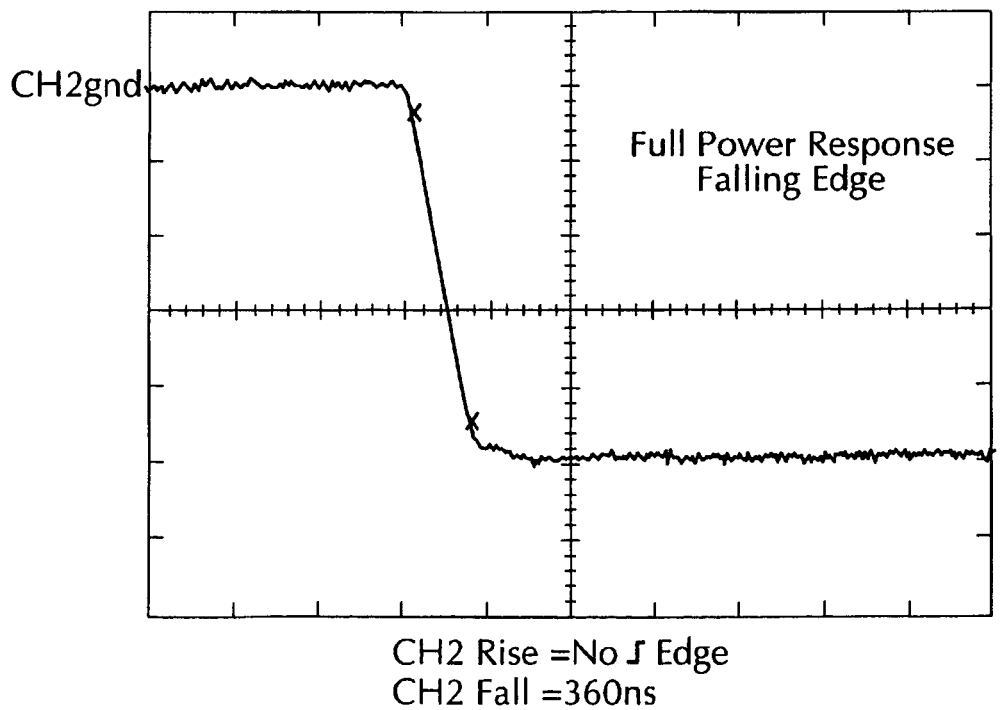
FIG. 4B is a graph showing at the full power output of an amplifier a pulse having a falling edge.

In the circuits shown in FIGS. 5 and 6, the output preferably varies from 0 to ±10 V and is set digitally. Rise time and fall time for a full power response in a standard speed implementation is 336 ns and 360 ns, respectively (see FIGS. 4A and 4B). For a 1.0 V pulse response, the corresponding numbers are 186 ns and 163 ns, respectively. The ES component can be also interfaced to a current output stage with single or multiple outputs and current levels of ±200 μA or another current level depending upon the particular application of use. In practice an isolated power supply for both analog and digital signals can be used.

An optional galvanic isolation can be added between the digital and analog parts of the ES component using standard electronic components. This isolation system, in combination with an isolated power supply for the analog signals, provides an isolated output from the stimulator.

1. Pulse Generation:

This aspect of the invention is a detailed solution for generating fast, high accuracy analog pulses with predefined pulse amplitudes, as well as for combining at least two single pulses to a pulse pattern. It is one of possible specific solutions which can be implemented as a part of the overall system design. The "Inputs and Outputs" section below can be viewed as a design example to show the concept behind creating an analog pulse pattern based on at least two pulse signals A and B. Each of the A and B pulses has a separate setting of the pulse width and pulse amplitude. The same concept is used to create a highly accurate biphasic or alternating pulses based on a single amplitude setting for both positive and negative part of the signal and thus eliminating the risk for an unbalanced charge delivered to the experimental system.

Digital pulses A and B have a pulse width TA and TB and a delay TD between them generated in hardware (or software) and together with the d-c voltages preset to the desired amplitudes for each pulse signal constitute the input signals to this stage. The design depicted in the "Inputs and Outputs" section uses a voltage reference and two 12-bit DACs on the same chip to set carefully controlled d-c levels. The digital pulses A and B are used to control opening and closing of a switch on the output of each of the DACS, respectively, and thus shaping A and B pulse waves. The correct amplitudes are set by the DACs and the correct analog pulse width is set by the length of time the appropriate analog switch is closed. When the switch is open, the output voltage for A and B pulse, respectively, is set to zero. Both waveforms are then passed through an adding circuitry. A d-c level can be added at the same time.

An optional set of preprogrammed modules, based on the architecture of the basic ES component, can be used independently or added to the basic ES component or even made a part of the ASIC design; for example, a pulse train used clinically for bone healing (timing parameters; repetition rate −15 Hz, pulse train length −5 ms, positive pulse with −200 us, negative pulse width −24 us, Electro-Biology, Inc. Parsippany, N.J.). This conventional bone-healing signal, measured with a pick-up coil, is delivered from an electromagnetic field (EMF) stimulator. A preprogrammed ES module allows for testing of the biological effects of the same or a similar electrical signal, but delivered through electrodes, without a strong magnetic field component, in addition to or instead of both experimental and clinical use in EMF stimulators. In situations with multiple parallel experiments, the cost of the equipment presently required will be significantly reduced by using pulse generator ASIC-based system of this invention rather than buying several independent stimulators.

The flexible pulse generator ASIC and the ES component of this invention can form the basis for an ES device as described herein, and can be used by electrical stimulation equipment manufacturers as an inexpensive off-the-shelf component to simplify production, cut costs, save space, and miniaturize existing systems. The present invention improves the overall system reliability by providing the whole system as a single well-tested component. The present invention using an ASIC reduces the power requirements, thus permitting battery operation in applications where high current/voltage output is not required, which also allows for a further miniaturization of the total digital/analog system and adds a safety feature for clinical applications.

The following are examples of signal generators that can be incorporated in the ES signal stage 10, and the respective variable timing parameters of these generators:

I. Pulse Generator (a) Square pulse—repetition rate (50% duty cycle)
(b) Single pulse A—repetition rate & pulse width (c) Dual pulses A and B—individually set pulse width single output: same repetition rate for both A and B; dual outputs: same or individually set repetition rates (d) Alternate pulse—set automatically by setting pulse A parameters (e) Biphasic pulse—set automatically setting pulse A parameters (f) A+B—same repetition rate for both individual pulse widths (g) A−B—same repetition rate for both, individual pulse widths (h) Pulse train—repetition rate of pulse train, and either pulse width of the pulse train or number of individual pulses in the train (i) User defined—all applicable timing parameters II. Sinewave generator—frequency III. Sawtooth, triangle, ramp waveform generators—frequency, rise and fall times IV. Arbitrary waveform generator—all timing parameters Inputs and Outputs:

Referring now to FIG. 5, (Sections A & B) there are two, 2 mm, 40 pin headers (P1 and P2) from which signal inputs, signal outputs, and power connect to the printed circuit board (pcb). The board requires two supplies to operate, +15 VDC and −15 VDC. Power and Ground comes in through P2. +5 VDC necessary for logic circuitry and interface is derived from onboard regulator U15 from the +15 VDC supply.

Figure 6A:
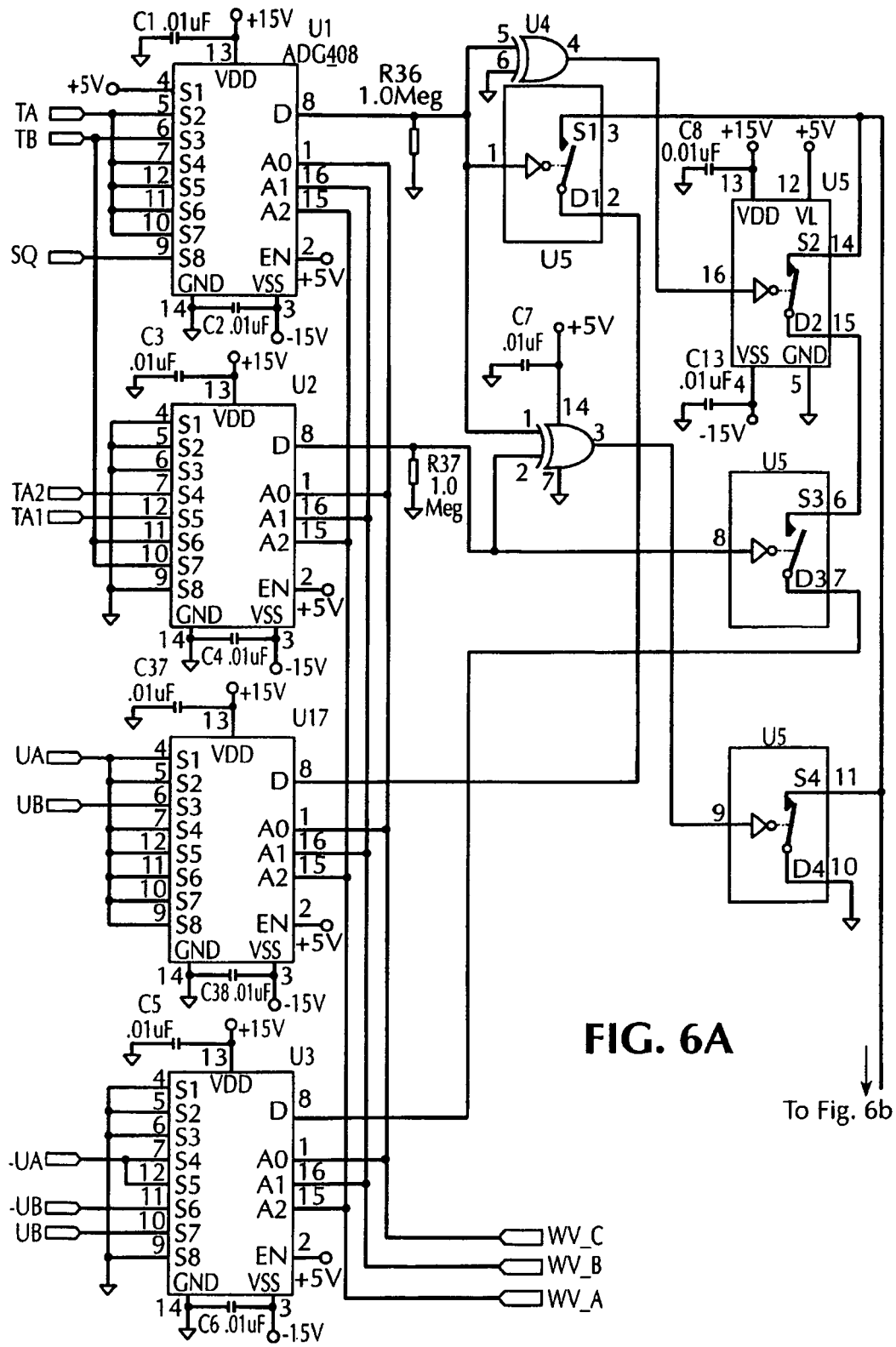

Referring now to FIG. 6A, pulse waveforms are generated within the stimulator by appropriate switching of 8 to 1 multiplexers U1, U2, U17, and U3. Logic level pulses TA, TB, SQ, TA1, and TA2 are selected by addressing U1 and U2 with signals WV-A, WV-B, and WV-C. U17 and U3 sets pulse polarity and select between UA and UB amplitudes.

TABLE 1

| WV-A | WV-B | WV-C | PULSE | AMPLITUDE |
|---|---|---|---|---|
| 0 | 0 | 0 | Constant "ON" | Constant UB |
| 0 | 0 | 1 | TA, "0" | Pulsed TA = UA |
| 0 | 1 | 0 | TB, "0" | Pulsed TB = UB |
| 0 | 1 | 1 | TA, TA2 | Pulsed TA = UA, TA2 = −UA |
| 1 | 0 | 0 | TA, TA1 | Pulsed TA = UA, TAI = −UA |
| 1 | 0 | 1 | TA, TB | Pulsed TA = UA, TB = −UB |
| 1 | 1 | 0 | TA, TB | Pulsed TA = UA, TB = UB |
| 1 | 1 | 1 | SQ, "0" | Pulsed SQ = UA |

U4 and U5 comprise the "logic" which creates the waveform and routes the resultant signal to the output amplifiers. When the output of U1 pin 8 is high, switch 1 of U5 is enabled, presenting the level determined by U17 to the output amplifiers, This also breaks switch 2 of U5 which prevents contention with the output of U3. The level determined by U3 pin 8 is presented to the output amplifiers when U1 pin 8 is low and U2 pin 8 is high. When U1 pin 8 and U2 pin 8 are low, corresponding to no pulses, switch 4 of U5 is enabled, thereby shorting the input of the output amplifiers to ground. This discharges or resets the node to 0 VDC.

Output Amplifiers:

The dual operation amplifier IC, U9, and associated passive components comprise the output amplifiers. Pin 2 of U9 is a summing junction. Pulses described above induce current through R3 into the inverting node of the first amplifier (pin 2). If DC_LEVEL is set, d-c voltage appearing at the junction of R4 and U8 pin 14 induces a d-c current into the same inverting junction thereby creating a d-c voltage bias level at the output. If DC-LEVEL is not set, R4 is grounded through switch 2 of U8. No d-c bias appears at the output in this case. OUT1 is the output of the first operational amplifier. This represents the inverted pulsed signal output train. The second amplifier of U9 is also an inverter which provides a non-inverted pulse train. Switches 3 and 4 of U8 allow for the polarity selection of OUT 2. A logic low selects the non-inverting output. A logic high selects the inverted output. Upon selecting the inverting output illuminates LED1.

D-C Level Circuits (FIG. 6B):

A 14 bit multiplying DAC, U6, operational amplifier U7, and associated passive components form the d-c level circuit. U6 is a current output DAC configured for bipolar output. The VREF input is determined by the level of UA. Since UA ranges from 0 to +10V, the d-c level circuit can range from 0 VDC to ±10 VDC. The 14-bit DAC bus interfaces directly to P1. Three control signals LVLDAC/LDAC, LVLDAC/CS, and LVLDAC/WR allow for addressing the DAC and writing levels. Refer to the AD75538 data sheet, for more detailed information on this part.

Figure 5A:
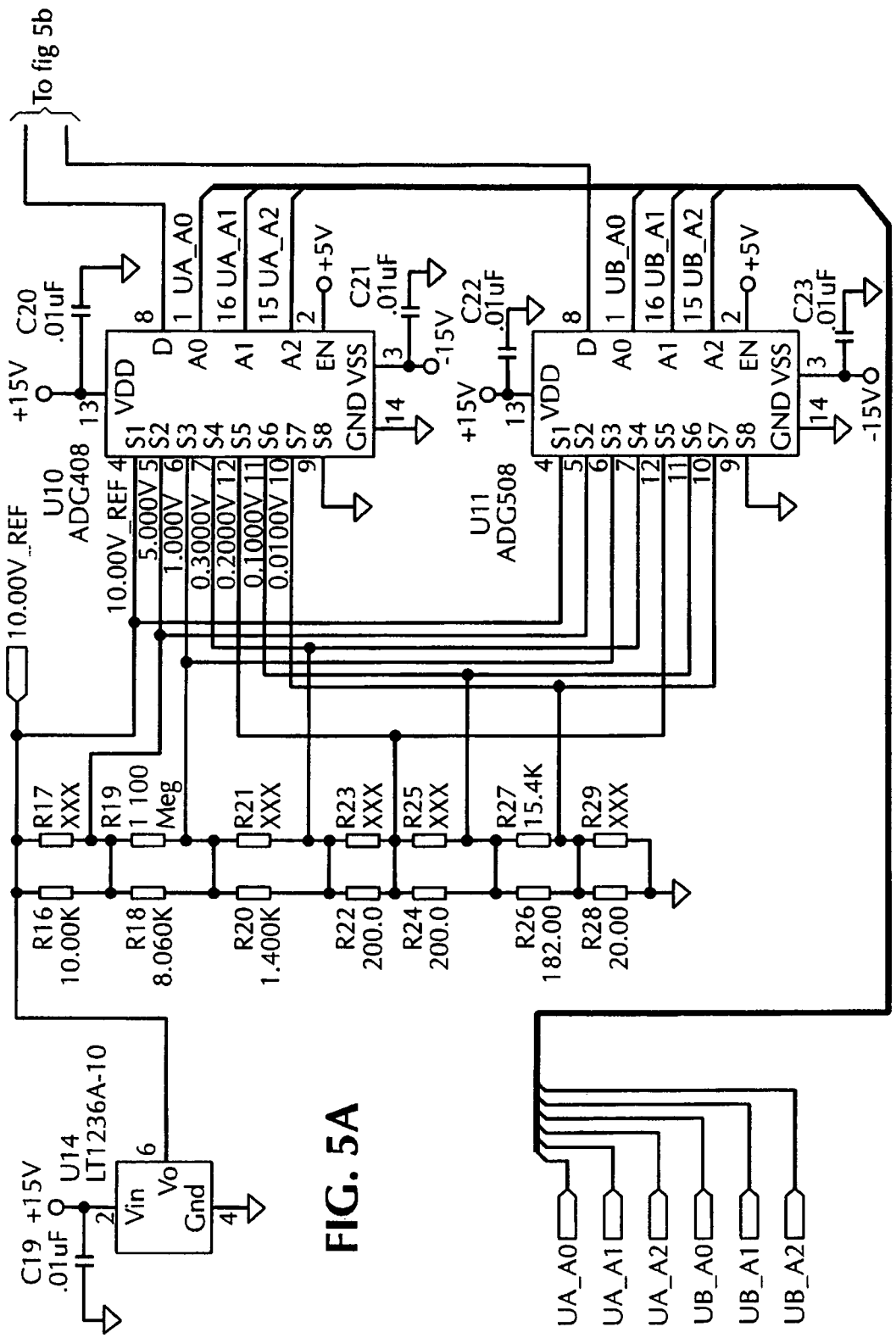
FIG. 5 (Sections A & B) and FIG. 6 (Sections A & B), show an embodiment of a low voltage output stage for generating various analog pulses and their combinations from digital inputs.
Figure 5B:
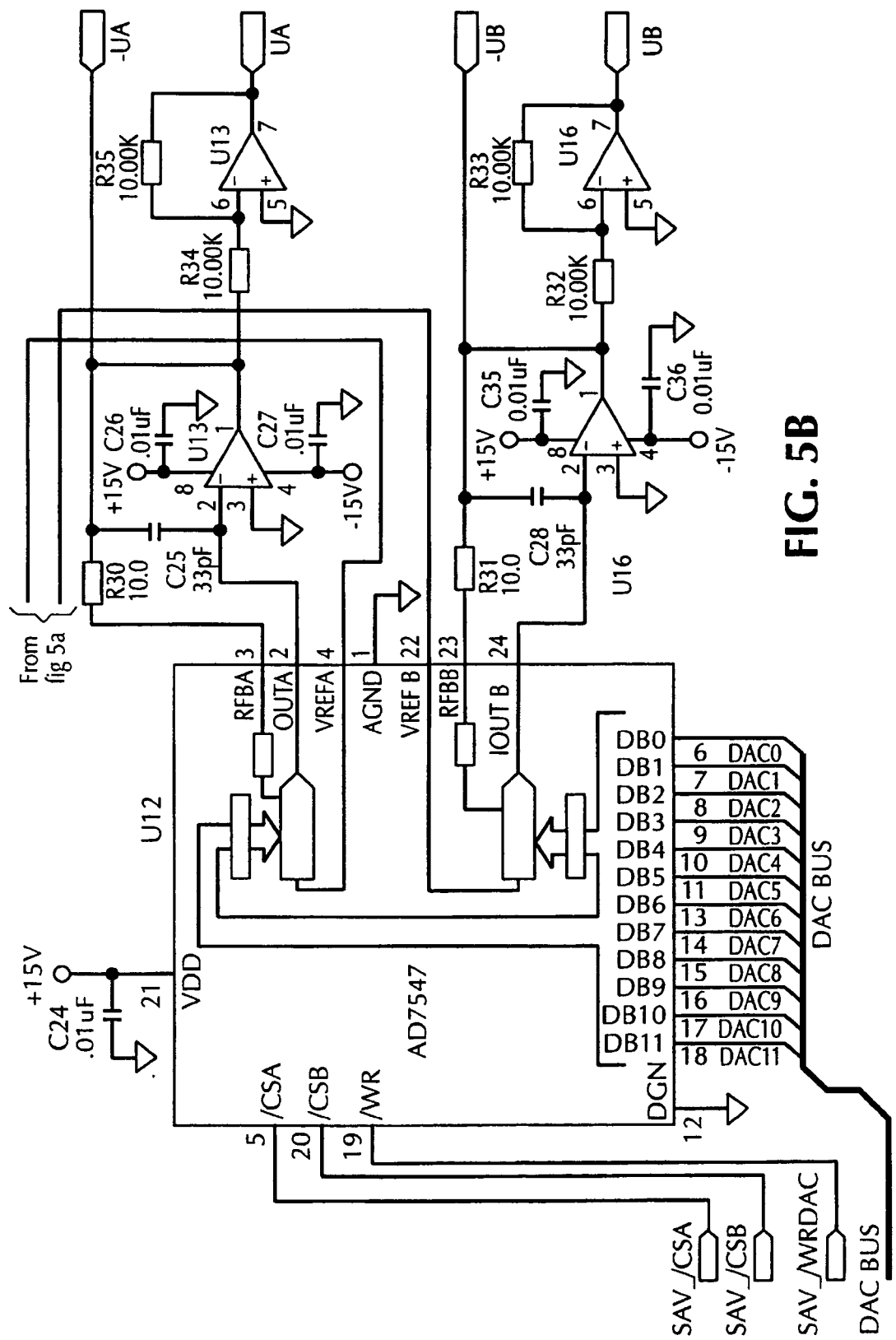
Figure 6B:
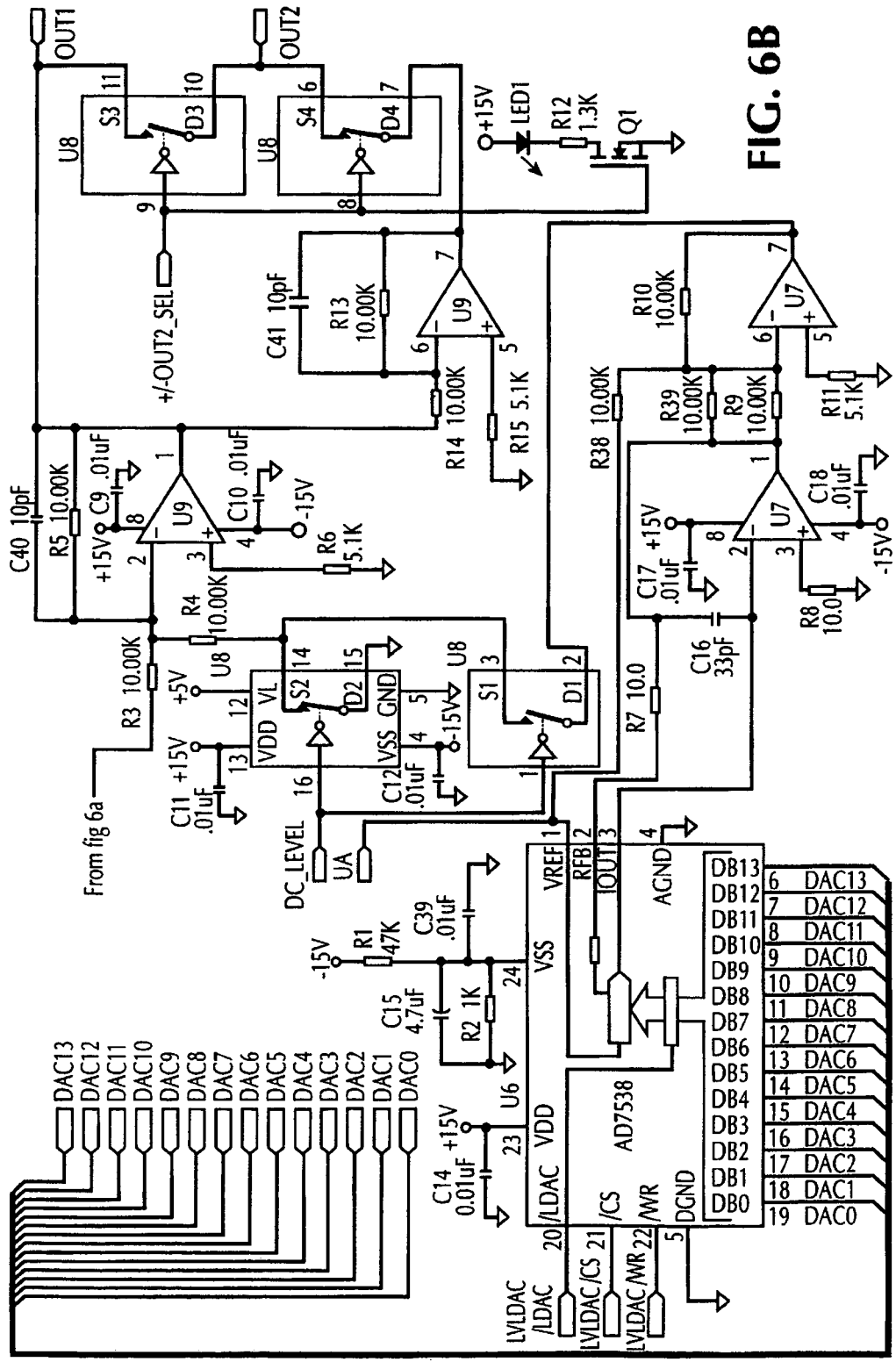

Dual Programmable Reference:

Referring now to FIG. 5A, U14 is an accurate and stable +10,00 volt reference, Resistors R16 through R29 form a precision resistive divider to derive 6 other voltage levels. U10 and U11 allow for the selection of +10,00V, 5.000V, 1.000V, 0.3000V, 0.2000V, 0.1000V, 0.0100V or ground for the UA and UB channels. Signals UA_AO, UA_A1, UA_A2 (Table 2), UB_AO, UB _A1, and UB_A2 (Table 3) determine the UA and UB reference levels respectively.

TABLE 2

| UA_AO | UA_A1 | UA_A2 | LEVEL |
|---|---|---|---|
| 0 | 0 | 0 | 10.00 V |
| 0 | 0 | 1 | 5.000 V |
| 0 | 1 | 0 | 1.000 V |
| 0 | 1 | 1 | 0.3000 V |
| 1 | 0 | 0 | 0.2000 V |
| 1 | 0 | 1 | 0.1000 V |
| 1 | 1 | 0 | 0.0100 V |
| 1 | 1 | 1 | 0.0000 V |

TABLE 3

| UB_AO | UB_A1 | UB_U2 | LEVEL |
|---|---|---|---|
| 0 | 0 | 0 | 10.00 V |
| 0 | 0 | 1 | 5.000 V |
| 0 | 1 | 0 | 1.000 V |
| 0 | 1 | 1 | 0.3000 V |
| 1 | 0 | 0 | 0.2000 V |
| 1 | 0 | 1 | 0.1000 V |

TABLE 3-continued

| UB_AO | UB_A1 | UB_U2 | LEVEL |
|---|---|---|---|
| 1 | 1 | 0 | 0.0100 V |
| 1 | 1 | 1 | 0.0000 V |

A dual op amp, U13, converts the DAC's A channel current output to +UA and −UA voltages. Likewise, U16 converts the DAC's B channel current output to +UB and −UB voltages. U12 is a dual 12-bit multiplying DAC arranged for unipolar outputs. U12 shares the same data bus (see FIGS. 5B and 6B) as U6. It is addressed and controlled by the SAV_/CSA, SAV_/CSB, and SAV_/WRDAC signals. ±UA and ±UB are used by the waveform generating circuits to set signal amplitude and polarity. The UA level is also used as the reference for the level DAC. Please refer to the datasheets for the AD7538, AD7547, ADG408, ADG433, AD712, 78LO5, and LT1235 components.

Voltage Output Stage:

A ±10V voltage output is a generic output stage useful for several neuromuscular and other applications. This output stage preferably includes an output amplifier stage sufficient to drive a load. A ±50V voltage output stage can be used in the alternative as a generic output stage useful for several neuromuscular and other applications. It can be limited to a lower voltage than the maximum ±50V by choosing a lower voltage power supply and changing values of appropriate components such as resistors. This higher voltage output stage is especially useful for the optimization of low voltage electroporation, and it can be packaged together with the ES component. Higher voltage output stages in the range up to 250V, or even higher up to 1,000V, or up to a few thousand volts (preferable about 6,000V), and ranges therebetween, can be used (or can be specially useful) for pulsed voltage electrophoresis or magnetic stimulation of the brain, 2. Magnetic Sensor Probe:

There is no good technique available on the market today to cover measurements of both time varying and constant magnetic fields in the range of 0-10 Gauss, or higher (often used in biomedical experiments as well as in clinical treatment—bone healing), and those that are available do not provide a reasonable bandwidth and resolution in three directions simultaneously. Magnetoresistive sensors, such as those pioneered by Honeywell, offer the various advantages over other forms of magnetic sensors, such as flux gates or coils: small dimensions, such as needed in biomedical applications; high sensitivity, allowing for a long distance between the item being sensed and the device (dependent on its ferromagnetic mass); immunity to electromagnetic noise and interferences due to the small internal impedance; and better reliability because it is a solid state solution with no moving parts; and lower development costs because components can be easily incorporated into board-level products.

A magnetic probe useful with the present invention is preferably a 3-axis magnetic sensor working in the range of 0 to 10 Gauss, preferably 0 to 20 Gauss, or 0 to 40 Gauss, with resolution better than 100 μGauss, and diameter of approximately 1 cm. Magnetoresistive transducers are made of long strips of thin ferromagnetic films of material such as per Malloy, a nickel-iron alloy. These films are deposited and fabricated using standard semiconductor technology on silicon wafers. The strips are several hundred Angstrom (150-500) in thickness, several tens of microns wide (10-50) and several hundred to several thousand microns long, and can be used to make the magnetic probe useful for this invention. An analog output magnetic sensor hybrid (e.g., model number HMC2003, available from Honeywell) is a "building block" product that allows to use an independent micro-controller, while obtaining the resolution and sensitivity of conventional magnetoresistive technology. (The Honeywell device comes in a small 20 pin 600 mil dual-in-line package that combines the magnetic sensing components with signal conditioning electronics and amplification for each channel.) To measure the field range of 0-10 Gauss, used in some electromagnetic stimulation experiments, and preferably 0-20 Gauss, the sensor can be used in a closed mode operation. In a further embodiment, the probe includes the ability to measure temperature. Another embodiment includes a miniature 3-axis probe (<3 mm in diameter) with amplification. Both these sensors can be utilized in both ac and dc mode.

3. System Overview:

Referring again to FIG. 1 showing the system composed of ES stage 10, output stage 11 and measuring stage 12, in using this system the user chooses the particular signal or waveform appropriate to the intended electrical stimulation application. The user uses a dial or switches attached to the system or software communicating with the system, and sets up specific timing and amplitude parameters via the serial or parallel input ports 18 and 19. The user also selects output stage 11 with either single or multiple output ports.

Measuring stage 12, by means of a sensor input terminal 12A, allows the use of appropriate sensors to sense the electrical stimulation signal passing through the organic substance being treated and environmental parameters, such as current, magnetic field, voltage, impedance, temperature, pH, gas ($O_2$, $CO_2$, etc.) as well as various biochemical substances involved locally in or resulting from the procedure at the site where the signal is administered or at another site.

The various sensors for this purpose include sensing electrodes, pick-up coils, temperature-sensitive devices, magnetic probes, and biosensors, all which yield a signal which is applied to input terminal 12A this terminal is connected to a signal conditioner 33 whose output is coupled to a measuring and display unit 34 whose output is fed to a video screen or other indicator. Associated with unit 34 is a display control 35 and a DMM control 36.

In some embodiments, the ES system may include an ES component comprising one or more signal generators and output circuitry packaged together. As described above, using a BCD parallel interface and a controller, pulse widths, pulse delays, and any other suitable electrical parameter may be independently configured for two different channels over six decades. An example of an ES component is shown and further described in Appendix A, which is attached hereto and incorporated by reference herein in its entirety.

In some embodiments, the ES component may be used with a board that allows a user to evaluate the characteristics of the ES component. The board may be configured to be electrically connected to the ES component. In addition, the board may also include other components, such as, for example, LED alphanumeric displays, switches, a prototyping area, etc.

The user may use the board to evaluate the performance, functionality, timing, and operations of the ES component.

However, although this board is generally described as being used for evaluation and/or prototyping, this is only illustrative. This board may also be, for example, integrated into subassemblies for system use.

In some embodiments, the evaluation board may have a VME form factor. In addition, the evaluation board may include a connector such that the board with the ES components or any other suitable pulse generation circuitry may be seamlessly integrated into a VME chassis or any other suitable chassis for use by the user.

The board for evaluating the ES component is further described in the above-referenced Appendix A.

In some embodiments, the ES system may include a general purpose output board. The general purpose output board may be used to allow a user to configure one or more ES components or other suitable electronic modules that are equipped to produce output signals. The general output board may include a plurality of user-operable switches (e.g., jumpers). Based on the position of each of the switches, the user may set one or more electrical parameters of the electronic module. Electrical parameters may include, for example, amplitude, frequency, shape, timing parameters, phase, pulse duration, and/or pulse repetition rate. The general purpose output board may be electrically connected to the electronic module via a connection to the evaluation board or by any other suitable approach.

The general purpose output board is further described in the above-reference Appendix A.

General System Features:

As ES system in accordance with the invention consists of a digital, high accuracy pulse generator capable of generating several either dependent or independent, synchronized rectangular pulses, available simultaneously, through a selector or preferably on a system bus. One or more output stages (identical or different) can be placed anywhere on the system bus and be accessed by a user. The choice the user makes may be threefold; either one specific output stage is plugged into the system; a specific output stage is selected among several output stages available using either a dial, a selector, or other means; or several output stages are used in parallel, either independently or triggered by each other.

The ES system can be also triggered by an external process or event, e.g., a physiological event, and will deliver either a preset signal in response to such a stimuli, or a signal which can be continuously modified by a triggering signal with respect to both timing and amplitude (and possibly shape). A preset delay between a triggering signal and a response signal can be made available.

Signals other than pulses can also be made available and accessible either through a selector or on the bus, including gated and/or modulated signals of various shapes. All of the signals can be fed to the output stages in the following ways: one signal to one output stage (with a single or multiple outputs); one signal to several output stages (identical or different); several signals to one output stage (for a complex signal shape or in case of multiple outputs); several signals to several output stages (identical or different).

Several, simple or complex rectangular pulses and other signals are available, for the output stages, through a selector or preferably on the bus. These signals are synchronized and can be accessed by an output stage either by selecting only one signal or by accessing several signals at the same time. In the latter case the signals can be combined in the output stage to a more complex pattern. In either case, they can be accessed by a single selected output stage or simultaneously by several, either identical or different, output stages.

By having a number of signals accessible on the bus, output stages can have simultaneous access to identical or different signals creating the following system configurations:

A. one selected output stage (either voltage—low or high, current-low or high, or power) with a single output producing a simple signal; one selected output stage with a single output producing a complex signal pattern;

B. one selected output stage with multiple identical outputs (either voltage—low or high, current—low or high, or power) with the same shape signals and identical electrical parameters; one selected output stage with multiple identical outputs with the same shape signals with different amplitudes only;

C. multiple identical output stages (either voltage—low or high, current—low or high, or power) with the same shape signals with identical electrical parameters; multiple identical output stages with the same shape signals with different amplitudes; multiple identical output stages with the same shape signals with different timing; multiple identical output stages the same shape signals with different amplitude and timing;

D. multiple identical output stages with different shape signals with all the options from above;

E. multiple identical output stages producing signals with either identical or different complex patterns with all the options from above;

F. multiple different output stages, e.g., a low voltage single output stage and multiple output current output stage, or a power output stage, producing the same shape signals with identical timing; multiple different output stages, producing the same shape signals with different timing; multiple different output stages, producing different shape signals with identical timing; multiple different output stages, producing different shape signals with different timing.

While there has been shown and described preferred embodiments of a multi-functional electrical stimulation system in accordance with the invention, it will be appreciated that many changes may be made therein within the spirit of the invention.

What is claimed is:

1. An electronic module equipped to produce an output signal, the electronic module comprising:
   a digital input interface that receives a set of digital input signals including timing parameters and amplitude parameters, wherein the timing parameters include one or more pulse width values, one or more delay time values, one or more repetition rate values, and an overall period for the set of digital input signals, wherein the timing parameters are each independently configurable by a user using the digital input interface for different channels that includes at least a first channel and a second channel;
   at least one pulse generator and one or more signal generators connected to the digital input interface and the at least one pulse generator that generate a plurality of synchronized signals that include the set of digital input signals, wherein at least one of the input signals has a timing parameter based on the one or more repetition rate values and the overall period and an amplitude parameter that are set by one of the timing parameters and the amplitude parameters received from the digital input interface, wherein at least one of the input signals has a pulse parameter set by the one or more pulse width values and the one or more delay time values of the timing parameters received from the digital input interface and processed by the at least one pulse generator, and wherein each of the plurality of synchronized signals are simultaneously provided for selection on the first and second channels; and a selection mechanism connected to the at least one pulse generator, and the one or more signal generators, and a plurality of output terminals, wherein the selection mechanism places a first signal of the plurality of synchronized signals on a first output terminal of the plurality of output terminals and places a second signal of the plurality of synchronized signals on a second output terminal of the plurality of output terminals, and wherein the first output terminal and the second output terminal are different output terminals.

2. The electronic module of claim 1, wherein the first signal on the first output terminal is independent from the second signal on the second output terminal.

3. The electronic module of claim 1, wherein the timing parameters include at least one of: a pulse train period or repetition rate, and a number of pulses in the pulse train.

4. The electronic module of claim 1, wherein the plurality of synchronized signals includes one or more: rectangular waves, sawtooth waves, sine waves, and arbitrary waves.

5. The electronic module of claim 1, wherein each of the plurality of synchronized signals has independently set periods or repetition rates.

6. The electronic module of claim 1, wherein the plurality of synchronized signals are identical.

7. The electronic module of claim 1, further comprising a port for accepting a signal from one or more sensors that sense conditions prevailing in at least one medium.

8. The electronic module of claim 7, wherein the one or more sensors comprise at least one of sensing electrodes, impedance measuring devices, pickup coils, temperature sensitive devices, magnetic probes, pH sensors, gas sensors, biochemical sensors, and biosensors.

9. The electronic module of claim 7, wherein the one or more sensors are used to monitor a condition for adjusting, using a feedback mechanism, at least one of the signals.

* * * * *